US012569493B2

(12) United States Patent
Geoffrion et al.

(10) Patent No.: US 12,569,493 B2
(45) Date of Patent: Mar. 10, 2026

(54) TREATMENT OF CHEMOSENSORY DYSFUNCTION FROM A CORONAVIRUS INFECTION

(71) Applicant: Cyrano Therapeutics, Inc., Delray Beach, FL (US)

(72) Inventors: Richard Geoffrion, Delray Beach, FL (US); Robert I. Henkin, Washington, DC (US)

(73) Assignee: Cyrano Therapeutics Inc., Delray Beach, FL (US)

( * ) Notice: Subject to any disclaimer, the term of this patent is extended or adjusted under 35 U.S.C. 154(b) by 742 days.

(21) Appl. No.: 17/913,191

(22) PCT Filed: Mar. 19, 2021

(86) PCT No.: PCT/US2021/023283
§ 371 (c)(1),
(2) Date: Sep. 21, 2022

(87) PCT Pub. No.: WO2021/194893
PCT Pub. Date: Sep. 30, 2021

(65) Prior Publication Data
US 2023/0147101 A1      May 11, 2023

Related U.S. Application Data

(60) Provisional application No. 63/006,489, filed on Apr. 7, 2020, provisional application No. 62/994,172, filed on Mar. 24, 2020.

(51) Int. Cl.
| | |
|---|---|
| *A61K 31/522* | (2006.01) |
| *A61K 9/00* | (2006.01) |
| *A61K 31/44* | (2006.01) |
| *A61K 31/4709* | (2006.01) |
| *A61K 45/06* | (2006.01) |
| *A61P 27/00* | (2006.01) |
| *A61P 31/14* | (2006.01) |

(52) U.S. Cl.
CPC .......... *A61K 31/522* (2013.01); *A61K 9/0043* (2013.01); *A61K 31/44* (2013.01); *A61K 31/4709* (2013.01); *A61K 45/06* (2013.01); *A61P 27/00* (2018.01); *A61P 31/14* (2018.01)

(58) Field of Classification Search
CPC .... A61K 31/522; A61K 9/0043; A61K 31/44; A61K 31/4709; A61K 45/06; A61P 27/00; A61P 31/14
See application file for complete search history.

(56) References Cited

U.S. PATENT DOCUMENTS

| | | |
|---|---|---|
| 174,915 A | 3/1876 | Lorenz |
| 4,066,405 A | 1/1978 | Henkin |
| 4,146,501 A | 3/1979 | Henkin |
| 4,368,197 A | 1/1983 | Shefter |
| 4,444,879 A | 4/1984 | Foster |
| 4,652,521 A | 3/1987 | Confer |
| 4,683,195 A | 7/1987 | Mullis |
| 4,683,202 A | 7/1987 | Mullis |
| 4,800,159 A | 1/1989 | Mullis |
| 4,992,445 A | 2/1991 | Lawter |
| 5,001,139 A | 3/1991 | Lawter |
| 5,023,252 A | 6/1991 | Hseih |
| 5,079,142 A | 1/1992 | Coleman |
| 5,132,324 A | 7/1992 | Meglasson |
| 5,169,849 A | 12/1992 | Kiechel |
| 5,384,308 A | 1/1995 | Henkin |
| 5,525,329 A | 6/1996 | Snyder |
| 5,591,645 A | 1/1997 | Rosenstein |
| 5,601,986 A | 2/1997 | Takacs |
| 5,614,627 A | 3/1997 | Takase |
| 5,622,871 A | 4/1997 | May |
| 5,707,802 A | 1/1998 | Sandhu |
| 5,714,993 A | 2/1998 | Keoshkerian |
| 5,788,967 A | 8/1998 | Henkin |
| 5,849,741 A | 12/1998 | Watanabe |
| 5,859,006 A | 1/1999 | Daugan |
| 5,869,516 A | 2/1999 | Arlt |
| 5,993,782 A | 11/1999 | Gardner |
| 6,207,703 B1 | 3/2001 | Ponikau |
| 6,228,660 B1 | 5/2001 | May |
| 6,387,639 B1 | 5/2002 | Posner |
| 6,462,044 B2 | 10/2002 | Garvey |

(Continued)

FOREIGN PATENT DOCUMENTS

| | | |
|---|---|---|
| EP | 0967214 B1 | 12/1999 |
| EP | 1547592 A1 | 6/2005 |

(Continued)

OTHER PUBLICATIONS

Wikipedia—Nebulizer; https://en.wikipedia.org/wiki/Nebulizer, obtained from the internet, Jun. 11, 2025, Internet Archive Wayback Machine Date Jan. 21, 2020. (Year: 2020).*
Otte, et al.; Acta Oto-Laryngologica, v140, pp. 1032-1035; 2020 (Year: 2020).*
Henkin, et al., Archives of Otolaryngology—Head & Neck Surgery, v138, pp. 1064-1079; 2012 (Year: 2012).*
Henkin, et al.; The American Journal of the Medical Sciences, v341, pp. 17-22; 2011 (Year: 2011).*
C. Huart et al., Comparison of COVID-19 and common cold chemosensory dysfunction, Rhinology, 2020, vol. 58, No. 6, p. 623-625.
PCT/US2021/023283 International Search Report and Written Opinion mailed Jul. 9, 2021.
PCTUS2006015846 International Search Report mailed Nov. 14, 2016.

(Continued)

*Primary Examiner* — Jeffrey S Lundgren
*Assistant Examiner* — W. Justin Youngblood
(74) *Attorney, Agent, or Firm* — Greenberg Traurig LLP

(57) ABSTRACT

Disclosed herein are methods of treating a taste and smell disorder caused by a viral infection in a subject, comprising administering to the subject a phosphodiesterase inhibitor. Also disclosed herein are methods of treating taste and smell loss from COVID-19 by administering a phosphodiesterase inhibitor to a subject in need thereof.

19 Claims, No Drawings

(56)                    References Cited

U.S. PATENT DOCUMENTS

| | | | |
|---|---|---|---|
| 6,506,801 | B1 | 1/2003 | Yee |
| 6,929,925 | B1 | 8/2005 | Zuker |
| 7,109,042 | B2 | 9/2006 | May |
| 7,144,585 | B1 | 12/2006 | Mukai |
| 7,670,849 | B2 | 3/2010 | Henkin |
| 8,293,489 | B2 | 10/2012 | Henkin |
| 8,506,934 | B2 | 8/2013 | Henkin |
| 8,549,741 | B2 | 10/2013 | Nelson |
| 8,580,801 | B2 | 11/2013 | Henkin |
| 8,663,938 | B2 | 3/2014 | Henkin |
| 8,968,706 | B2 | 3/2015 | Henkin |
| 9,719,988 | B2 | 8/2017 | Henkin |
| 10,206,927 | B2 | 2/2019 | Henkin |
| 11,125,760 | B2 | 9/2021 | Henkin |
| 11,774,458 | B2 | 10/2023 | Henkin |
| 2003/0055039 | A1 | 3/2003 | Ikeya et al. |
| 2004/0209843 | A1 | 10/2004 | Inoue |
| 2005/0288265 | A1 | 12/2005 | Locher |
| 2006/0222718 | A1 | 10/2006 | Böhme et al. |
| 2006/0275801 | A1 | 12/2006 | Henkin |
| 2007/0190103 | A1 | 8/2007 | Hossainy |
| 2008/0029084 | A1 | 2/2008 | Costantino |
| 2008/0200484 | A1 | 8/2008 | Liu |
| 2008/0318913 | A1 | 12/2008 | Fox |
| 2009/0299190 | A1 | 12/2009 | Burns |
| 2010/0022563 | A1 | 1/2010 | Henkin |
| 2010/0227875 | A1 | 9/2010 | Henkin |
| 2011/0023870 | A1 | 2/2011 | Wermeling |
| 2011/0137407 | A1 | 6/2011 | Nguyen |
| 2011/0151393 | A1 | 6/2011 | Frey, II |
| 2011/0166166 | A1 | 7/2011 | Henkin |
| 2012/0178768 | A1 | 7/2012 | Henkin |
| 2013/0011849 | A1 | 1/2013 | Henkin |
| 2013/0144372 | A1 | 6/2013 | Wood |
| 2013/0225595 | A1 | 8/2013 | Gillies |
| 2014/0053835 | A1 | 2/2014 | Gilbert |
| 2014/0073654 | A1 | 3/2014 | Henkin |
| 2014/0105977 | A1 | 4/2014 | Devarakonda |
| 2015/0297601 | A1 | 10/2015 | Henkin |
| 2015/0366869 | A1* | 12/2015 | Henkin ................. G01N 33/576 514/263.34 |
| 2016/0030435 | A1 | 2/2016 | Henkin |
| 2017/0227548 | A1 | 8/2017 | Henkin |
| 2019/0224426 | A1 | 7/2019 | Farina |
| 2019/0231785 | A1 | 8/2019 | Henkin |
| 2019/0350934 | A1 | 11/2019 | Henkin |
| 2020/0375974 | A1 | 12/2020 | Henkin |
| 2021/0060316 | A1 | 3/2021 | Stankus |
| 2021/0300963 | A1 | 9/2021 | Cavanagh |
| 2022/0087938 | A1 | 3/2022 | Sävmarker |
| 2022/0226332 | A1 | 7/2022 | Henkin |

FOREIGN PATENT DOCUMENTS

| | | |
|---|---|---|
| EP | 1035833 B1 | 8/2005 |
| NL | 2031214 B1 | 9/2023 |
| WO | 199626940 A1 | 9/1996 |
| WO | 9641194 A1 | 12/1996 |
| WO | 9703675 A1 | 2/1997 |
| WO | 199703985 A1 | 2/1997 |
| WO | 199743287 A1 | 11/1997 |
| WO | 199817668 A1 | 4/1998 |
| WO | 199849166 A1 | 11/1998 |
| WO | 1999001135 A1 | 1/1999 |
| WO | 199921562 A1 | 5/1999 |
| WO | 199930697 A2 | 6/1999 |
| WO | 0148477 A1 | 7/2001 |
| WO | 0182931 A1 | 11/2001 |
| WO | 03025224 A1 | 3/2003 |
| WO | 03025224 A3 | 3/2003 |
| WO | 2006085102 A1 | 8/2006 |
| WO | 2006119292 A2 | 11/2006 |
| WO | 2007044375 A2 | 4/2007 |
| WO | 2008141438 A1 | 11/2008 |
| WO | 2009003199 A1 | 12/2008 |
| WO | 2009115235 A1 | 9/2009 |
| WO | 2010147981 A1 | 12/2010 |
| WO | 2012016845 A3 | 2/2012 |
| WO | 2012016889 A3 | 2/2012 |
| WO | 2012154975 A3 | 11/2012 |
| WO | 2013021199 A2 | 2/2013 |
| WO | 2014055801 A1 | 4/2014 |
| WO | 2014059197 A1 | 4/2014 |
| WO | 2014143453 A1 | 9/2014 |
| WO | 2015126944 A1 | 8/2015 |
| WO | 2015136515 A1 | 9/2015 |
| WO | 2015194962 A1 | 12/2015 |
| WO | 2017095219 A1 | 6/2017 |
| WO | 2017095220 A1 | 6/2017 |
| WO | 2018026812 A1 | 2/2018 |
| WO | 2018034920 A1 | 2/2018 |
| WO | 2019006173 A1 | 1/2019 |
| WO | 2019136306 A1 | 7/2019 |
| WO | 2020160037 A1 | 8/2020 |
| WO | 2021194893 A1 | 9/2021 |
| WO | 2021255622 A1 | 12/2021 |

OTHER PUBLICATIONS

PCTUS2013063331 International Search Report Written Opinion mailed Dec. 12, 2013.

PCTUS2013064416 International Search Report and Written Opinion mailed Dec. 5, 2013.

PCTUS2014014940 International Search Report Written Opinion mailed Apr. 8, 2014.

PCTUS2015016381 International Search Report Written Opinion mailed May 29, 2015.

Pace, U., Hanski, E., Salomon, Y, et al. Odorant-sensitive adenylate cyclase may mediate olfactory reception. Nature. 1985, vol. 316, p. 255-8.

Papthanassiu, A., Henkin, R.I. cAMP is present in human nasal mucus and may act as a growth factor in cells of the olfactory epithelium. FASEB J. 2002, vol. 16, A1153.

Pelangaris, et al. Oncogenic co-operation in beta-cell tumorigenesis. Endocr Relat Cancer. Dec. 2001, vol. 8(4), p. 307-14.

Philips, et al. Factors determining the appearance of glucose in upper and lower respiratory tract secretions. Intensive Care Med. Dec. 2003, vol. 29(12), p. 2204-10.

Poehling, et al., Accuracy and Impact of a Point of a Care Rapid Influenza Test in Young Children With Respiratory Illnesses, Arch Pediatr Adolsec Med., 2006, vol. 160(7), p. 713-718.

Rickli, E.E., et al., Carbonic Anhydrases from Human Erythrocytes, J. Biol. Chem., 1964, vol. 239, p. 1065-1078.

Riste, et al. High prevalence of Type 2 diabetes in all ethnic groups, including Europeans, in a British Inner City. Diabetes Care, 2001, vol. 24, p. 1377-1383.

Rock, et al. Inhibitors of the proteosome block the degradation of most cell proteins and the generation of peptides presented on MHC class 1 molecules. Cell. 1994, vol. 78, p. 761-771.

Rosenzweig S., Yan, W., Sasso, M., et al. Possible novel mechanism for bitter taste mediated through cGMP. J. Neurophysiol. 1999, vol. 81, p. 1661-5.

Sano, et al. Immuno-PCR: Very sensitive antigen detection by means of specific antibody—DNA conjugates. Science, vol. 258 (1992), p. 120-122.

Schaeffer L.D ., Sproles, A, Krakowski, A Detection of cAMP in parotid saliva of normal individuals. J. Dent. Res. 1973, vol. 52, p. 629.

Schechter P.J., Friedwald, W.T., Bronzert, D.A., Raff, M.S., Henkin, R.I. Idiopathic hypogeusia: a description of the syndrome and a single blind study with zinc sulfate, in Intemat. Rev. Neurobiol. Suppl. 1., (Pfeiffer, C., Ed.), Academic Press, NY, 1972, pp. 125-133.

Schechter, P.J. et al., Abnormalities of Taste and Smell Following Head Trauma. J. Neurol. Neurosurg. Psychiat., 1974, vol. 37, p. 802-810.

(56)                    References Cited

OTHER PUBLICATIONS

Schiffman, et al. Methyl xanthines enhance taste: evidence for modulation of taste by adenosine receptor. Pharmacol Biochem Behav, Feb. 1985, vol. 22(2), p. 195-203.

Seal, et al. Point-of-care nucleic acid lateral flow tests. IVD Techology, 2006, pp. 41-51.

Seiden A.M., Duncan, H.J., Smith, D.V. Office management of taste and smell disorders. Otolaryngol. Clin. North Amer. 1992, vol. 25, p. 817-835.

Shepherd Shepherd, G.M. Sensory transduction entering the mainstream of membrane signaling. Cell. 1991; vol. 67, p. 845-851.

Shin, et al. Virus-induced Type 1 IFN stimulates generation of immunoproteasomes at the site of infection. J. Clin. Invest. 2006, vol. 116(11), p. 3006-3014.

Shirley, et al. Olfactory adenylate cyclase of the rat. Stimulation by odorants and inhibition by Ca2+. Biochem J, Dec. 1, 1986, vol. 240(2), p. 605-7.

Sklar, et al. The odorant-sensitive adenylate cyclase of olfactory receptor cells. Differential stimulation by distinct classes of odorants. J Biol Chem. Nov. 25, 1986, vol. 261 (33), p. 15538-43.

Sobottka, et al. Disseminated Encephalitozoon (Septata) intestinalis infection in a patient with AIDS: novel diagnostic approaches and autopsy-confirmed parasitological cure following treatment with albendazole. J Clin Microbial. Nov. 1995, vol. 33(11), p. 2948-52.

Spivey, et al. Comparative Analysis of Manual Versus Automated Actuation Parameters for Droplet Size Determination by Laser Diffraction for Spray Devices. Catalent Pharma Solutions. 2008. 1 page.

Suzuki. Proceedings of the 21st Japanese Symposium on Taste and Smell: cyclic nucleotides as intracellular messengers in the olfactory transduction process. Chem Sense. 1988, vol. 13, Abstract.

Temmel, A.F.P., et al., Characteristics of Olfactory Disorders in Relation to Major Causes of Olfactory Loss. Arch. Otolaryngol. Head Neck Surg. 2002; vol. 128; pp. 635-641.

The Expert Committee. Report of the Expert Committee on the Diagnosis and Classification of Diabetes Mellitus. Diabetes Care. 2003, vol. 26, S5-S20.

Thompson, W.J. Cyclic nucleotide phosphodiesterase: pharmacology, biochemistry and function. Pharmacol. Ther. 1991, vol. 51, p. 13-33.

Vaughan. Second wind for second-messenger research. Bioscience. 1987, vol. 37, p. 642-646.

Velicu, et al. Insulin is present in human saliva and nasal mucus. Journal of Investigative Medicine. 2006, vol. 54, S385.

Velicu, I., et al., On the Antiapoptotic Mechanism of Action of Theophylline in Restoring Smell Function in Patients with Hyposmia, J. Invest. Med., 2005, vol. 53 (Suppl. 2), S402.

Voegels, et al. Expression of interleukins in patients with nasal polyposis. Otolaryngology—Head and Neck Surgery, 2005, vol. 132, No. 4, p. 613-616.

Washington et al., Determination of baseline human nasal pH and the effect of intranasally administered buffers, International Journal of Pharmaceutics, vol. 198, 2000, p. 139-146.

Weinstock, et al. Olfactory dysfunction in humans with deficient guanine nucleotide-binding protein. Nature, Aug. 14-20, 1986, vol. 322(6080), p. 635-6.

Weyer, et al. The natural history of insulin secretory dysfunction and insulin resistance in the pathogenesis of type 2 diabetes mellitus. J Clin Invest, Sep. 1999, vol. 104(6), p. 787-94.

Will, et al. Cigarette smoking and diabetes mellitus from a large prospective cohort study. Int. J. Epidemiol, 2001, vol. 30, p. 540-546.

Williams, G. Diabetes. In Endocrine Disorder. Oxford Testbook of Medicine. vol. 2, 4th Edition, Oxford Univ. Press 2003, p. 317-359.

Wood, et al. Effect of hyperglyaemia on glucose concentration of human nasal secretions. Clin Sci (Lond). May 2004, vol. 106(5), p. 527-33.

Wysocki C.J., Gilbert, A.N. National Geographic Smell Survey: Effects of age are heterogeneous. Ann. NY Acad. Sci. 1989, vol. 561, p. 12-28.

Chai et al., Two nights of recovery sleep restores hippocampal connectivity but not episodic memory after total sleep deprivation, Scientific Reports, 2020, vol. 10, p. 1-11.

Henkin et al., Sonic Hedgehog in Nasal Mucus is a Biomarker for Smell Loss in Patients with Hyposmia, Cellular & Molecular Medicine, 2016, vol. 2, p. 1-6.

International Search Report and Written Opinion for PCT/US2024/025817 mailed Sep. 23, 2024.

Last et al., Scaling toward Diminutive MEMS: Dust-Sized Spray Chips for Aerosolized Drug Delivery to the Lung, Advanced Materials, 2023, vol. 8, No. 7, p. 1-8.

Myatt et al., Unlocking further understanding of the atomization mechanism of a pressurized metered dose inhaler, Aerosol Science and Technology, 2022, vol. 56, No. 11, p. 1-11.

Sheng et al., Inhibition of phosphodieterase: A novel therapeutics target for the treatment of mild cognitive impairment and Alzheimer's disease, Front Aging Neurosci., 2022, vol. 14, p. 1-12.

Si et al., Liquid Film Translocation Significantly Enhances Nasal Spray Delivery to Olfactory Region: A Numerical Stimulation Study, Pharmaceuticals, 2021, vol. 13, p. 1-19.

Henkin R.I.et al., Hypogeusia, dysgeusia, hyposmia and dysosmia following influenza-like infection. Ann. Otol. Rhin. Laryngol. 1975, vol. 8, p. 672-682.

Henkin R.I.et al., A zinc protein isolated from human parotid saliva. Proc. Nat. Acad. Sci. USA 1975, vol. 72, p. 488-492.

Henkin R.I.et al., Decreased parotid salivary cyclic nucleotides related to smell loss severity in patients with taste and smell dysfunction. Metabolism Clinical and Experimental, 2009 p. 1717-1723.

Henkin RI, et al. 'Intranasal Theophylline Treatment of Hyposmia and Hypogeusia,' Arch Otolaryngol Head Neck Surg, (2012) vol. 138 No 11, pp. 1064-1070.

Henkin RI, et al., Olfactory Hallucinations Without Clinical Motor Activity: a Comparison of Unirhinal with Birhinal Phantosmia. Brain Sci. 2013, vol. 3, p. 1483-1553.

Henkin RI, et al., Taste and smell function in chronic disease: a review of clinical and biochemical evaluation of taste and smell dysfunction in over 5000 patients at the Taste and Smell Clinic in Washington, DC. Amer. J Otolaryngology. 2013, vol. 4, p. 477-489.

Henkin Robert, et al., Rapid changes in taste and semll function following transcranical magnetic stimulation (TCMS) in humans: relationships to CNS plasticity, FASEB J., 2002, vol. 16, A878.

Henkin, et al. Aberrant signaling in the olfactory system: a mechanism for smell loss. FASEB Journal, vol. 18, No. 4-5, pp. Abst. 792.7, 2004.

Henkin, et al. Interleukin 6 in hyposmia. JAMA Otolaryngol Head Neck Surg, Jul. 2013, vol. 139(7), p. 728-34.

Henkin, et al. Treatment of abnormal chemsensation in human taste and smell. In: Norris DM, ed. Perception of Behavioral Chemicals. Amsterdam, Netherlands: Elsevier/North Holland Biomedical Press, 1981, p. 227-265.

Henkin, et al., Insulin receptors as well as insulin are present in saliva and nasal mucus. Journal of Investigative Medicine, 2006, vol. 54, (Suppl. 2), S378.

Jenkin, R.I. et al., cAMP and cGMP in Nasal Mucus: Relationships to Taste and Smell Dysfunction, Gender and Age. Clinical Invest. Med. 2008, vol. 3, E71-E77.

Henkin, R.I. et al., Effective Treatment of Smell Loss with Theophylline. Exper. Biol., 2008, vol. 22, B976.2.

Henkin, R.I. et al., Is Increased IL-6 the Result or Cause of Smell Loss in Patients with Hyposmia?, FASEB Journal, 2009, vol. 23 (Meeting Abstract Supplement), Abstract 835.1.

Henkin. Concepts of therapy in taste and smell dysfunction: repair of sensory receptor function as primary treatment. Olfaction and Taste XI, (Kurihara, K., Suzuki, N., Ogawa, H., Eds.), Springer Verlag, 1994, pp. 568-573.

Huque, et al. Odorant- and guanine nucleotide-stimulated phosphoinositide turnover in olfactory cilia. Biochem Biophys Res Commun. May 29, 1986, 137(1), p. 36-42.

Inthavong, et al., A Numerical Study of Spray Particle Deposition in a Human Nasal Cavity, Aerosol Science and Technology, vol. 40(11), p. 1034-1045.

(56)             References Cited

OTHER PUBLICATIONS

Kanamori, T. et al., Origin of cyclic adenosine monophosphate in saliva. J. Dent. Res. 1975, vol. 54, p. 535-539.

Kim, et al. Defects in the peripheral taste structure and function in the MRL/lpr mouse model of autoimmune disease. PLoS One, 2012, vol. 7(4), e35588.

Kragelund, et al. N-terminal Pro-B-type natriuretic-peptide and long-term mortality in stable coronary heart disease. New Engl. J. Med. 2006, vol. 252, p. 666-675.

Kublik, et al. Nasal delivery systems and their effect on deposition and absorption. Adv Drug Deliv Rev. Jan. 5, 1998, vol. 29(1-2), p. 157-177.

Kulkarni, et al. Formulation and characterization of nasal sprays. An examination of nasal sprat formulation parameters and excipients and their influence on key in vitro tests. Inhalation, Jun. 2012, p. 10-15.

Kundoor et al., Effect of Formulation- and Administration-Related Variables on Deposition Pattern of Nasal Spray Pumps Evaluated Using a Nasal Cast, Pharm Res, 2011, vol. 28, p. 1895-1904.

Kurihara, K., Koyama, N. High activity of adenylyl cyclase in olfactory and gustatory organs. Biochem. Biophys. Rev. Comm. 1972, vol. 48, p. 30-34.

Kurihara, K., Suzuki, N., Ogawa, H., Eds.), Concepts of Therapy in Taste and Smell Dysfunction: Repair of Sensory Receptor Function as Primary Treatment, Springer Verlag, 1994, pp. 568-573.

Lancet, et al. Molecular transduction in smell and taste. Cold Spring Harb Symp Quant Biol. 1988, vol. 53, Pt 1, p. 343-8.

Law, et al. Distribution of calmodulin in taste buds. Life Sci, 1985, vol. 36, p. 1189-1195.

Law, et al. Zinc deficiency decreases the activity of calmodulin regulated cyclic nucleotide phosphodiesterases in vivo in selected rat tissues. Biol Trace Elem Res, Aug. 1988, vol. 16(3), p. 221-6.

Law, et al., Low parotid saliva calmodulin in patients with taste and smell dysfunction. Biochem Med Metab Biol, Aug. 1986, vol. 36(1), p. 118-24.

Lee, et al. Thiolated chitosan nanoparticles enhance anti-inflammatory effects of intranasally delivered theophylline. Respir Res., Aug. 24, 2006, vol. 7, p. 1-10.

Levine, et al. Soluble endoglin and other circulating antiangiogenic factors in preeclampsia. New Engl. J. Medicine. 2006, vol. 355, p. 992-1005.

Levy L.M., Henkin, R.I., Hutter, A, Lin, C.S., Schellinger, D. Increased brain activation in response to odors in patients with hyposmia after theophylline treatment demonstrated by fMRI. J. Comp. Asst. Tomog. 1998, vol. 22, p. 760-770.

Lindheimer, et al. Explaining and predicting preeclampsia. New Engl. J. Medicine. 2006, vol. 355, p. 1056-1058.

Liu Hong Xiang et al.: "Multiple Shh Signaling Centers Participate in Fungiform Papilla and Taste Bud Formation and Maintenance", Developmental Biology, vol. 382, No. 1, Aug. 2, 2013 (Aug. 2, 2013), pp. 82-97.

Liu, et al., "Sonic Hedgehog Exerts Distinct, Stage-Specific Effects on Tongue and Taste Papilla Development", Development Biology, vol. 276, pp. 280-300, Sep. 25, 2004.

Lowe, et al. Contribution of the ciliary cyclic nucleotide-gated conductance to olfactory transduction in the salamander. J Physiol. Mar. 1993, vol. 462, p. 175-96.

Lu et al., Hydrogen sulfide regulates cAMP homeostasis and renin degranulation in As4.1 and rat renin-rich kidney cells, Cell Physiology, 2012, vol. 302, C59-C66.

Maggi et al., TT Virus in the Nasal Secretions of Children with Acute Respiratory Diseases: Relations to Viremia and Disease Severity, J Virology, Feb. 2003, vol. 77(4), p. 2418-2425.

Maitra, et al. The pancreas in Pathological Basis of Disease. 7th Edition. Elsevier, 2004, p. 1155-1207.

Margolskee, Robert F. Molecular mechanisms of taste transduction. Pure and applied chemistry, 2002, vol. 74(7), p. 1125-1133.

Margolskee. The biochemistry and molecular biology of taste transduction. Curr Opin Neurobiol, Aug. 1993, vol. 3 (4), p. 526-31.

Mcauley, et al. Diagnosing insulin resistance in the general population. Diabetes Care. Mar. 2001, vol. 24(3), p. 460-4.

Meret, S., et al., Simultaneous Direct Estimation by Atomic Absorption Spectrophotometry of Copper and Zinc in Serum, Urine, and Cerebrospinal Fluid, Clin. Chem., 1971, vol. 17, pp. 369-373.

Misaka, et al. Taste buds have a cyclic nucleotide-activated channel, CNGgust. J Biol Chem, Sep. 5, 1997, vol. 272 (36), p. 22623-9.

Moharram R., et al., Meeting Abstracts, FASEB J., 2004, 18:A201.

Moon, C. et al., Regulation of Intracellular Cyclic GMP Levels in Olfactory Sensory Neurons. J. Neurochem., 2005, vol. 95, p. 200-9.

MWV Healthcare MK Sprayer. Product Information. 2013. 2 pages.

Nakajima, et al. Studies on cyclic nucleotides in brochopulmonary diseases with special reference to cAMP, cGMP in patients with nasal allergy and bronchial asthma. Acta Med. Kinki Univ., 1979, vol. 4, p. 257-272.

Nakamura, et al. Proceedings of the 25th Japanese Symposium on Taste and Smell: 1. Current and Ca influx induced by intracellular cAMP in the newt olfactory receptor. Chem Sense, 1991, vol. 17, p. 85-116.

Neumann, S. et al., Regeneration of Sensory Axons Within the Injured Spinal Cord Induced by Intraganglionic cAMP Elevation. Neuron., 2002, vol. 34, p. 885-893.

Henkin et al., Improved Smell and Taste Dysfunction with Intranasal Theophylline, American Journal of Otolaryngology and Head and Neck Surgery, Remedy Publications LLC, 2019, vol. 2, Issue 9, Art 1070, p. 1-8.

Wall et al., Pentoxifylline or theophylline use in hospitalized COVID-19 patients requiring oxygen support, Clin Respir J., 2021, Viol 15, p. 843-846.

Agarwal, et al., Bio. Tr. Elem. Res., 1985, vol. 7, pp. 199-208.

Ajani, et al. Alcohol consumption and risk of coronary heart disease by diabetes status. Circulation. Aug. 1, 2000, vol. 102(5), p. 500-505.

Anderson, et al., Handbook of Clinical Drug Data, Tenth Edition, McGraw-Hill, 2002.

Anholt, R.R.H. Molecular neurobiology of olfaction. Crit. Rev. Neurobiol. 1993, vol. 7, p. 1-22.

Asakura, K., Kataura, A cAMP and cGMP in the human parotid saliva. Arch. Otorhinolaryngol. 1980, vol. 226, p. 1529-30.

Atkinson, et al., The pathogenesis of insulin-dependent diabetes mellitus. New Engl. J. Med. 1994, vol. 33, p. 1428-1436.

Bakalyar, et al. Identification of a specialized adenylyl cyclase that may mediate odorant detection. Science. Dec. 7, 1990, vol. 250(4986), p. 1403-6.

Bogardus, et al. Relationships between insulin secretion, insulin action, and fasting plasma glucose concentration in nondiabetic and noninsulin-dependent diabetic subjects. J Clin Invest. Oct. 1984, vol. 4(4), p. 1238-46.

Borisy, et al. High-affinity cAMP phosphodiesterase and adenosine localized in sensory organs. Brain Res. May 7, 1993, vol. 610(2), p. 199-207.

Breer. Molecular reaction cascades in olfactory signal transduction. J Steroid Biochem Mol Biol. Oct. 1991, vol. 39(4B), p. 621-5.

Bromley, S.M. Smell and taste disorders: a primary care approach. Amer. Fam. Physician., 2000, vol. 61, p. 427-436.

Cai, D. et al., Neuronal Cyclic AMP Controls the Developmental Loss in Ability of Axons to Regenerate. J. Neurosci., 2001, vol. 21, p. 4731-4739.

Cai, D. et al., Prior Exposure to Neurotrophins Blocks Inhibition of Axonal Regeneration by MAG and Myelin via a cAMP Dependent Mechanism. Neuron., 1999, vol. 22, p. 89-101.

Carlsson, et al. Alcohol consumption and the increase of Type II diabetes: Finnish twin cohort study. Diabetes Care. 2003, vol. 26, p. 2785-2790.

Cho HJ, et al. 'Development of Udenafil-Loaded Microemulsions for Intranasal Delivery: In Vitro and in Vivo Evaluations,' International Journal of Pharmaceutics, (2012) vol. 423, pp. 153-160.

Chou. Wake up and smell the coffee. Caffeine, coffee, and the medical consequences. West J Med. Nov. 1992, vol. 157(5), p. 544-53.

Church J.A., Bauer, H., Bellanti, J.A., Satterly, R.A., Henkin, R.I. Hyposmia associated with atopy. Ann. Aller. 1978, vol. 40, p. 105-109.

(56) References Cited

OTHER PUBLICATIONS

Cicinelli, P., et al., Post-stroke reorganization of brain motor output to the hand: a 2-4 month follow-up with focal magnetic transcranial stimulation, Eletroenceph. Clin. Neurophys, 1997, vol. 105, p. 438-450.

Cullen, M., Leopold, D. Disorders of smell and taste. Med. Clin. North Amer. 1999, vol. 83, p. 57-74.

Davidson, T.M., Murphy, C., Jalowayski, A.A Smell impairment: can it be reversed? Postgrad. Med. 1995, vol. 98, pp. 107-109, 112-118.

Deems, D.A., Doty, R.L., Settle, R.G., Moore-Gillon, V., Shaman, P., Mester, A.F., Kimmelman, C.P., Brightman, V.J., Snow, J.B. Jr. Smell and taste disorders, a study of 750 patients from the University of Pennsylvania Smell and Taste Center. Arch. Otolaryngol. Head Neck Surg. 1991, vol. 177, p. 519-528.

Djordjevic et al., Effects of Perceived and Imagined Odors on Taste Detection, Chem Senses, 2004, vol. 29, p. 199-208.

Doerty, A.E., Matin, B.M., Dai, W.L., Henkin, R.I. Carbonic anhydrase (CA) activity in nasal mucus appears to be a marker for loss of smell (hyposmia) in humans. J. Invest. Med. 1997, vol. 45,237A.

Doty, et al. Human odor intensity perception: correlation with frog epithelial adenylate cyclase activity and transepithelial voltage response. Brain Res. Sep. 10, 1990, vol. 527(1), p. 130-4.

Draheim, et al., Anti-Inflammatory Potential of the Selective Phosphodiesterase 4 Inhibitor N-(3,5-Dichloro-pyrid-4-yl)-[1-(4-fluorobenzyl)-5-hydroxy-indole-3-yl]-glyoxylic Acid Amide (AWD 12-281) in Human Cell Preparations, The Journal of Pharmacology and Experimental Therapeutics, vol. 308(2), p. 555-563.

Elshafeey AH, et al. 'Intranasal Microemulsion of Sildenafil Citrate: In Vitro Evaluation and In Vivo Pharmacokinetic Study in Rabbits, AAPS PharmSciTech, (2009), vol. 10, No. 2, pp. 361-367.

Firestien B.I., Bredt, D.S. Regulation of sensory neuron precursor proliferation by cyclic GMP-dependent protein kinase. J. Neurochem. 1998, vol. 71, p. 1846-1853.

Firestien S., Zufall, F., Sheperd, G.M. Single odor-sensitive channels in olfactory receptor neurons are also gated by cyclic nucleotides. J. Neurosci. 1991, vol. 11, p. 3565-72.

Franz, et al., Evidence-based nutrition principles and recommendations for diabetes and related complications. Diabetes Care, 2002, vol. 25, 1244-1265.

Gillespie, et al. Pharmacologic Management of Chronic Rhinosinusitis, Alone or with Nasal Polyposis. Current Allergy and Asthma Reports, 2004, vol. 4, No. 6, pp. 478-485.

Glenert, U., Geisler, A A single assay for cyclic adenosine 3':5'-monophosphate in human saliva. J. Cyclic Nucleotide Protein Phosphor. Res. 1985, vol. 10, p. 451-461.

Guidance for Industry. Nasal Spray and Inhalation Solution, Suspension, and Spray Drug Products—Chemistry, Manufacturing, and Controls Documentation. US Department of Health and Human Services. CDER. Jul. 2002.

Hardwick, et al., The effect of PGI2 and theophylline on the response of platelets subjected to shear stress. Blood. Oct. 1981, vol. 58(4), p. 678-81.

Harris R., Davidson, T.M., Murphy, C., Gilbert, P.E., Chem, M. Clinical evaluation and symptoms of chemosensory impairment: one thousand consecutive cases from the Nasal Dysfunction Clinic in San Diego. Amer. J. Rhinol. 2006, vol. 20, p. 101-108.

Henkin et al., Drug-induced taste and smell disorders, Drug safety, vol. 11, p. 310-377, 1994.

Henkin et al., Evaluation and treatment of human olfactory dysfunction, Otolaryngology, 1993, vol. 2, p. 1-64.

Henkin et al., Nasal seroproteins: a new frontier in the exploration of physiology and pathology of nasal and sinus disease, New Frontiers in Immunobiology, 2000, pp. 127-152.

Henkin R.I. Effects of ACTH, adrenocorticosteroids and thyroid hormone on sensory function, in Anatomical Neuroendocrinology, (Stumpf, W.E., Grant, L.D., Eds.), Karger, A.G. , Basel, 1975, pp. 298-316.

Henkin R.I. The definition of primary and accessory areas of olfaction as the basis for a classification of decreased olfactory acuity, in Olfaction and Taste II, (Hayashi, T. Ed.), Pergamon Press, London, 1967, pp. 235-252.

Henkin R.I. The role of adrenal corticosteroids in sensory processes, in Adrenal Gland, (Blaschko, H., Sayers, G., Smith, A.D., Eds.), Handbook of Physiology. Endocrinology, Washington, DC. Amer. Physiol. Soc., Sect. 7, vol. VI, 1975, pp. 209-230.

Henkin R.I. Zinc, saliva and taste: Interrelationships of gustin, nerve growth factor, saliva and zinc, in Zinc and Copper in Clinical Medicine, (Hambidge, K.M., Nichols, B.L., Eds.), Spectrum Publ. Inc., Jamaica, NY, 1978, pp. 35-48.

Henkin R.I. et al., Age related changes in cyclic nucleotides in saliva and nasal mucus—possible feedback mechanism in development of gustatory and olfactory receptor function. FASEB J. 2005, vol. 19, A1368.

Henkin R.I. et al., Idiopathic hypogeusia with dysgeusia, hyposmia and dysosmia: a new syndrome. J. Amer. Med. Assoc. 1971, vol. 217, p. 434-440.

Henkin R.I. et al., A Dichotomous changes in cAMP and cGMP in human parotid saliva after oral theophylline. FASEB J. 2003, vol. 17, A1028.

Henkin R.I. et al., cAMP and cGMP in Nasal Mucus Related to Severity of Smell Loss in Patients with Smell Dysfunction. Clinical Invest. Med., 2008, vol. 31, E78-E84.

Henkin R.I. et al., Decreased parotid saliva gustin/carbonic anhydrase VI secretion: an enzyme disorder manifested by gustatory and olfactory dysfunction. Amer. J. Med. Sci. 1999, vol. 318, p. 380-391.

Henkin R.I. et al., Efficacy of exogenous zinc in treatment of patients with carbonic anhydrase VI deficiency. Amer. J. Med. Sci. 1999, vol. 318, p. 392-404.

Henkin R.I., et al., A double blind study of the effects of zinc sulfate on taste and smell dysfunction, Amer. J. Med. Sci., 1976, vol. 272, p. 285-299.

Henkin R.I., et al., An Open-Label Controlled Trial of Theophylline for Treatment of Patients with Hyposmia, American Journal of Medical Sciences, vol. 337, No. 6, 2009, p. 396-406.

Dewey et al., Intranasal Apomorphine Rescue Therapy for Parkinsonian "Off" Periods, Clinical Neuropharmacology, 1996, vol. 19, No. 3, p. 193-201.

Gao et al., Factors influencing drug deposition in the nasal cavity upon delivery via nasal sprays, Journal of Pharmaceutical Investigation, 2020, vol. 50, p. 251-259.

Henkin et al., Taste and Smell Phantoms Revealed by Brain Functional MRI (fMRI), Journal of Computer Assisted Tomography, 2000, vol. 24, No. 1, p. 106-123.

International Search Report and Written Opinion for PCT/US2022/081622, mailed Jun. 9, 2023.

International Search Report and Written Opinion for PCT/US2022/081646, mailed Jun. 6, 2023.

International Search Report and Written Opinion for PCT/US2023/060164, mailed Apr. 6, 2023.

International Search Report and Written Opinion for PCT/US2023/060165, mailed Jun. 15, 2023.

International Search Report and Written Opinion for PCT/US2023/060168, mailed Jun. 14, 2023.

Khani et al., Potential pharmacologic treatments for COVID-19 smell and taste loss: A compreshensive review, European Journal of Pharmacology, 2021, vol. 912, p. 1-9.

Partial International Search Report and Provisional Opinion for PCT/US2023/060165, mailed Apr. 25, 2023.

Prakasam et al., Biodegradable Materials and Metallic Implants—A Review, J Funct Biomater, 2017, vol. 8(4), p. 1-15.

Provisional Opinion accompanying Partial Search Report for PCT/US2023/060168, mailed Apr. 20, 2023.

Shital et al., Development and Evaluation of a Novel Intranasal Spray for the Delivery of Amantadine, Journal of Pharmaceutical Sciences, 2016, vol. 105, p. 1209-1220.

Verma et al., Topical gels as drug delivery systems: A review. Int. J. Pharm. Sci. Rev. Res, 2013, vol. 23(2), p. 374-382.

(56)                    References Cited

OTHER PUBLICATIONS

Xi et al., Visualization and Quantification of Nasal and Olfactory Deposition in a Sectional Adult Nasal Airway Cast, Pharm Res, 2016, vol. 33, p. 1527-1541.
Yang et al., Reservoir-based polymer drug delivery systems. Journal of laboratory automation, 2012, vol. 17(1), p. 50-58.
Zhu et al., Delivery of theophylline as dry powder for inhalation, Asian Journal of Pharmaceutical Sciences, 2015, vol. 10, p. 520-527.
Costantino et al., Intranasal delivery: Physicochemical and therapeutic aspects, ScienceDirect, International Journal of Pharmaceuticals, 2007, vol. 337, p. 1-24.

* cited by examiner

TREATMENT OF CHEMOSENSORY DYSFUNCTION FROM A CORONAVIRUS INFECTION

CROSS-REFERENCE

This application claims priority to United States Provisional Patent Application Nos. 62/994,172, filed Mar. 24, 2020 and U.S. Provisional Patent Application No. 63/006, 489, filed Apr. 7, 2020, each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

SUMMARY

Disclosed herein are methods for treating chemosensory dysfunction in a human wherein the chemosensory dysfunction can be at least in part produced from, or occurring during or after, a coronavirus infection. In some embodiments, a method can comprise administering to a human a therapeutically effective amount of a phosphodiesterase (PDE) inhibitor or a pharmaceutically acceptable salt thereof to treat a chemosensory dysfunction. In some embodiments, (i) a coronavirus can comprise SARS-CoV-2 or a mutated form thereof, (ii) a PDE inhibitor or pharmaceutically acceptable salt thereof can be administered in a formulation in unit dose form; or (iii) any combination thereof. In some embodiments, a therapeutically effective amount of a PDE inhibitor or a pharmaceutically acceptable salt thereof can be formulated as a liquid formulation, a solid formulation, or a gel formulation. In some embodiments, a PDE inhibitor or a pharmaceutically acceptable salt thereof can be formulated as a liquid formulation and administering can comprise application of the liquid formulation as a nasal wash. In some embodiments, a PDE inhibitor or a pharmaceutically acceptable salt thereof can be formulated as a liquid formulation and administering can comprise application of the liquid formulation as an aerosol. In some embodiments, a PDE inhibitor or a pharmaceutically acceptable salt thereof can be formulated as a solid formulation and administering can comprise application of a solid formulation as a powder aerosol. In some embodiments, a PDE inhibitor or a pharmaceutically acceptable salt thereof can be formulated as a gel formulation and administering can comprise application of the gel formulation by contacting at least part of a naris with the gel formulation. In some embodiments, administering can comprise application of a liquid formulation, a solid formulation or a gel formulation intranasally in one nostril or both nostrils. In some embodiments, administering can be performed during or after a coronavirus infection. In some embodiments, a method can further comprise a second administering. In some embodiments, a second administering can comprise remdesivir, chloroquine, lopinavir, ritonavir, favilavir, interferon-beta, antivirals, oxygen or any combination thereof. In some embodiments, administering can be at least once, twice, or thrice within a 24-hour period. In some embodiments, chemosensory dysfunction can comprise anosmia, hyposmia, ageusia, dysosmia, parosmia, phantosmia or any combination thereof. In some embodiments, a PDE inhibitor or pharmaceutically acceptable salt thereof can be theophylline or a pharmaceutically acceptable salt thereof, roflumilast or a pharmaceutically acceptable salt thereof, cilostazol or a pharmaceutically acceptable salt thereof, a derivative of any of these or a pharmaceutically acceptable salt thereof, or any combination thereof. In some embodiments, a therapeutically effective amount can comprise a positive amount of less than about 100 mg, less than about 10 mg, less than about 1 mg, less than about 500 μg or less than about 100 μg of a PDE inhibitor or a pharmaceutically acceptable salt thereof. In some embodiments, administering of a PDE inhibitor or a pharmaceutically acceptable salt thereof can produce a blood concentration of the PDE inhibitor or the pharmaceutically acceptable salt thereof less than about 10 mg/dl, less than about 1 mg/dl, or less than about 100 μg/dl during a time course of the treating. In some embodiments, a PDE inhibitor or a salt thereof can comprise theophylline or a pharmaceutically acceptable salt thereof. In some embodiments, after the administering and during a time course of the treating, theophylline, a theophylline metabolite, an N-demethylated theophylline, or any combination thereof, can be present in blood in an amount of less than about 10 mg/dl, less than about 1 mg/dl, or less than about 100 μg/dl. In some embodiments, salivary or nasal mucus cAMP or cGMP levels in a human can increase by at least about 10% relative to these levels in the human before the administering, after about 30 days of continuous treatment with a therapeutically effective amount of a PDE inhibitor or pharmaceutically acceptable salt thereof. In some embodiments, smell acuity can increase by at least about 5% in a human, as measured by detection threshold (DT), relative to these levels in the human before the administering, after about 30 days of continuous treatment with a therapeutically effective amount of a PDE inhibitor or pharmaceutically acceptable salt thereof. In some embodiments, smell acuity can increase by at least about 5% in a human, as measured by recognition threshold (RI), relative to these levels in the human before the administering, after about 30 days of continuous treatment with a therapeutically effective amount of PDE inhibitor or pharmaceutically acceptable salt thereof. In some embodiments, smell acuity can increase by at least about 5% in a human, as measured by magnitude estimation (ME), relative to these levels in the human before the administering, after about 30 days of continuous treatment with a therapeutically effective amount of a PDE inhibitor or pharmaceutically acceptable salt thereof. In some embodiments, smell acuity can increase by at least about 5% in a human, as measured by hedonics (H), relative to these levels in the human before the administering, after about 30 days of continuous treatment with a therapeutically effective amount of a PDE inhibitor or pharmaceutically acceptable salt thereof. In some embodiments, chemosensory dysfunction can be diagnosed by detecting sonic hedgehog at or below a threshold level in a biological sample from the human, by detecting cyclic nucleotide level at or below a threshold level in the biological sample from the human, or any combination thereof. In some embodiments, chemosensory dysfunction can be diagnosed by determining a detection threshold, by determining a recognition threshold, and by magnitude estimation for at least one of: pyridine, nitrobenzene, thiophene, and amyl acetate. In some embodiments, a formulation can comprise an excipient. In some embodiments, an excipient can comprise water. In some embodiments, a PDE inhibitor or pharmaceutically acceptable salt thereof can be administered in the formulation in unit dose form. In some embodiments, a unit dose formulation can be contained within a multi-dose nasal spray device that delivers the unit dose in a plume upon actuation. In some embodiments, a plume can have a droplet size distribution. In some embodiments, a droplet size distribution can comprise (a) less than about 5% of the droplets in the plume having a size of less than about 10 μm, (b) a D10 of greater than about 12.5 μm, wherein about 10% of the droplets in the plume can have a size less than the D10, (c) a D50 of about 30 μm, wherein about 50% of the droplets in the plume can have a size less than the D50, (d) a D90 of about 75 μm to about 100 μm, wherein about 90% of the droplets in the plume can have a size less than the D90, and (e) a span of from about 1 to about 6, wherein the span can be calculated according to: (D90–D10)/D50. In some embodiments, a PDE inhibitor or a pharmaceutically acceptable salt thereof can be theophylline or a pharmaceutically acceptable salt thereof. In some embodiments, a human can be assigned male or female at birth. In some embodiments, a human can be from about 1 month to about 12 months old, from about 1 year to about 20 years, from about 15 years to about 50 years, from about 40 years to about 80 years, or from about 60 years to about 110 years. In some embodiments, a human can have a comorbidity. In some embodiments, a comorbidity can be selected from the group consisting of schematic heart disease, hypertension, atrial fibrillation, stroke, renal failure, liver disease, cancer, diabetes, respiratory diseases, and any combination thereof. In some embodiments, a comorbidity can be a respiratory disease. In some embodiments, a respiratory disease can be selected from asthma, chronic obstructive pulmonary disease, bronchitis, emphysema, lung cancer, cystic fibrosis, pneumonia, pleural effusion, or any combination thereof. In some embodiments, a coronavirus infection can be from a SARS-CoV-2 virus, a SARS-COV virus, a MERS-CoV virus, a HKU1 virus, a OC43 virus, a NL63 virus, a 229E virus, or any combination thereof.

DETAILED DESCRIPTION

Unless otherwise indicated, open terms for example "contain," "containing," "include," "including," and the like mean comprising.

Disclosed herein are methods of treatment by administering to a subject a phosphodiesterase (PDE) inhibitor, its salt, or a combination of PDE inhibitors or their salts. As disclosed herein, the term "PDE inhibitor" can refer to a compound that can at least partially inhibit the function of a PDE polypeptide, such as a PDE1, PDE2, PDE3, PDE4, PDE5 polypeptide, or any combination thereof.

PDE2 polypeptides can decrease aldosterone secretion. Such decrease may play an important role in the regulation of elevated intracellular concentrations of cAMP and cGMP in platelets. Several regions of the brain can express PDE2 and rat experiments indicate that inhibition of PDE2 can enhance memory. PDE2 may play a role in regulation of fluid and cell extravasation during inflammatory conditions as PDE2 can be localized to microvessels, especially venous capillary and endothelial cells. PDE2 may also be a good pharmacological target for pathological states such as sepsis or in more localized inflammatory responses such as thrombin-induced edema formation in the lung.

The PDE3 family hydrolyzes cAMP and cGMP, but in a manner suggesting that in vivo, the hydrolysis of cAMP can be inhibited by cGMP. They can also be distinguished by their ability to be activated by several phosphorylation pathways including the PKA and PI3K/PKB pathways. PDE3A can be relatively highly expressed in platelets, as well as in cardiac myocytes and oocytes. PDE3B can be a major PDE in adipose tissue, liver, and pancreas, as well as in several cardiovascular tissues. Both PDE3A and PDE3B can be highly expressed in vascular smooth muscle cells and are likely to modulate contraction. PDE5 can be a regulator of vascular smooth muscle contraction best known as the molecular target for several well-advertised drugs used to treat erectile dysfunction and pulmonary hypertension. In the lung, inhibition of PDE5 can oppose smooth muscle vasoconstriction, and PDE5 inhibitors are in clinical trials for treatment of pulmonary hypertension.

Examples of a PDE inhibitor can include, for example, filaminast, piclamilast, rolipram, Org 20241, MCI-154, roflumilast, toborinone, posicar, lixazinone, zaprinast, sildenafil, pyrazolopyrimidinones, motapizone, pimobendan, zardaverine, siguazodan, CI-930, EMD 53998, imazodan, saterinone, loprinone hydrochloride, 3-pyridinecarbonitrile derivatives, denbufyllene, albifylline, torbafylline, doxofylline, theophylline, pentoxofylline, nanterinone, cilostazol, cilostamide, MS 857, piroximone, milrinone, aminone, tolafentrine, dipyridamole, papaverine, E4021, thienopyrimidine derivatives, triflusal, ICOS-351, tetrahydropiperazino[1,2-b]beta-carboline-1,4-dione derivatives, carboline derivatives, 2-pyrazolin-5-one derivatives, fused pyridazine derivatives, quinazoline derivatives, anthranilic acid derivatives, imidazoquinazoline derivatives, and the like. In some embodiments, a one or more PDE inhibitors, or their salts, can be formulated in an intranasal composition. In some embodiments, the composition can comprise a non-specific PDE inhibitor or its salt. In some embodiments, the composition can comprise an PDE inhibitor or its salt that is selective for a PDE subtype, for example, PDE: 1, 2, 3, 4, or 5. In some embodiments, the intranasal composition does not comprise a PDE5 selective inhibitor. In some embodiments, the composition can be in a liquid, power, solid, or gel form. In some embodiments, the PDE inhibitor or its salt can be dosed at a range from about 0.001 mg to about: 1 mg, 2 mg, 3 mg, 4 mg, 5 mg, 6 mg, 7 mg, 8 mg, 9 mg, or 10 mg. In some embodiments, the formulation can be in unit dose form. In some embodiments, the formulation can contain a second active ingredient, such as a corticosteroid, or an antihistamine, or a vasoconstrictor, or any combination thereof. In some embodiments, the formulation does not contain a second active ingredient. In some cases, a formulation can be a pharmaceutical composition. In some cases, a composition can be a pharmaceutical composition.

A PDE inhibitor can be a selective PDE inhibitor, or a non-specific PDE inhibitor. A PDE selective inhibitor can include a PDE1 selective inhibitor, PDE2 selective inhibitor, PDE3 selective inhibitor, PDE4 selective inhibitor, or PDE5 selective inhibitor. In some cases, a selective PDE inhibitor can be specific for more than one of PDE1, PDE2, PDE3, PDE4, and PDE5. A non-specific PDE can include a PDE inhibitor that inhibits at least two, three, four, or five of PDE1, PDE2, PDE3, PDE4, and PDE5.

A PDE inhibitor can inhibit cellular apoptosis by inhibiting TNF alpha, TRAIL and their metabolites. PDE inhibitors can activate the production and secretion of nitric oxide in all tissues thereby inducing vasorelaxation or vasodilation of all blood vessels including those of the peripheral blood vessels (inhibiting intermittent claudication), the distal extremities and in the penile region contributing to penile erection.

A non-specific PDE inhibitor can include theophylline, papaverine caffeine, IBMX (3-isobutyl-1-methylxanthine, aminophylline, doxophylline, cipamphylline, theobromine, pentoxifylline (oxpentifylline) and diprophylline. Theophylline is a methylxanthine derivative that, when administered as described herein, can have anti-inflammatory effects on the airways that can be useful to combat the abnormal inflammation seen in asthmatics. In some cases, an anti-inflammatory effect can be achieved when theophylline is prescribed at or administered at levels that produce systemic levels of theophylline in the blood well below that which causes side effects. Patients with emphysema and chronic bronchitis can also be helped with theophylline when their symptoms are partially related to reversible airway narrowing.

A PDE1 selective inhibitor, formerly known as calcium- and calmodulin-dependent phosphodiesterases, can include ebumamenine-14-carboxylic acid ethyl ester (vinpocetine). In some cases, vinpocetine can be used to induce vasore-laxtion on cerebral smooth muscle tissue.

A PDE2 selective inhibitor can include EHNA (erythro-9-(2-hydroxy-3-nonyl) adenine), 9-(6-phenyl-2-oxohex-3-yl)-2-(3,4-dimethoxybenzyl)-purin-6-one (PDP), and BAY 60-7750.

A PDE3 selective inhibitor can include enoximone, milrinone (Primacor), amrinone, cilostamide, cilostazol (Pletal) and trequinsin. A PDE3 inhibitor when administered as described herein can produce sympathetic stimulation to increase cardiac inotropy, chronotropy and dromotropy. A PDE3 inhibitor when administered as described herein can also antagonize platelet aggregation, increase myocardial contractility, and enhance vascular and airway smooth muscle relaxation. PDE3A can be a regulator of this process. A PDE3 inhibitor when administered as described herein can effectively prevent aggregation. Cilastazol (Pletal), is approved for treatment of intermittent claudication. Its mechanism of action may involve inhibition of platelet aggregation along with inhibition of smooth muscle proliferation and vasodilation.

A PDE4 selective inhibitor can include mesembrine, rolipram, Ibudilast (i.e. a neuroprotective and bronchodilator drug that can be used in the treatment of asthma and stroke), and roflumilast (Daxas) and cilomilast (Airflo) (i.e. PDE4 selective inhibitors that can be administered for treatment of chronic obstructive pulmonary disease). A PDE4 selective inhibitor can at least partially suppress release of inflammatory mediators e.g., cytokines, or at least partially inhibit production of reactive oxygen species and immune cell infiltration. A PDE4 inhibitor can also be used to treat asthma, arthritis, and psoriasis.

A PDE5 selective inhibitor can include Sildenafil, tadalafil, vardenafil, udenafil and avanafil.

Definitions

The singular forms "a", "an", and "the" are used herein to include plural references unless the context clearly dictates otherwise. Accordingly, unless the contrary is indicated, the numerical parameters set forth in this application are approximations that can vary depending upon the desired properties sought to be obtained.

As used herein, the term "about" or "approximately" can mean within an acceptable error range for the particular value as determined by one of ordinary skill in the art, which will depend in part on how the value is measured or determined, e.g., the limitations of the measurement system. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges. The term "substantially" as used herein can refer to a value approaching 100% of a given value. In some cases, the term can refer to an amount that can be at least about 90%, 91%, 92%, 93%, 94%, 95%, 96%, 97%, 98%, 99%, 99.9%, or 99.99% of a total amount. In some cases, the term can refer to an amount that can be about 100% of a total amount.

The terms "administer," "administering", "administration," and the like, as used herein, can refer to methods that can be used to enable delivery of compounds or their salts or compositions to the desired site of biological action. Delivery can include direct application to the affect tissue or region of the body. A composition provided herein can be administered by any method. A method of administration can be by inhalation, intraarterial injection, intracerebroventricular injection, intracisternal injection, intramuscular injection, intraorbital injection, intraparenchymal injection, intraperitoneal injection, intraspinal injection, intrathecal injection, intravenous injection, intraventricular injection, stereotactic injection, subcutaneous injection, or any combination thereof. Delivery can include parenteral administration (including intravenous, subcutaneous, intrathecal, intraperitoneal, intramuscular, intravascular or infusion), oral administration, nasal administration, inhalation administration, intraduodenal administration, rectal administration. Delivery can include topical administration (such as a lotion, a cream, a gel, a liquid, a solid, a powder, an ointment) to an external surface of a surface, such as a skin. In some instances, a subject can administer the compound, salt thereof, or composition in the absence of supervision. In some instances, a subject can administer the composition under the supervision of a medical professional (e.g., a physician, nurse, physician's assistant, orderly, hospice worker, etc.). In some cases, a medical professional can administer the composition. In some cases, a cosmetic professional can administer the composition.

As used herein, "treating" of chemosensory dysfunction can include one or more of: reducing the frequency or severity of one or more symptoms, elimination of one or more symptoms or their underlying cause, or improvement or remediation of damage. For example, treatment of chemosensory dysfunction can include, for example, increasing smell acuity and taste acuity from a patient suffering from a Coronavirus infection, such as a patient with COVID-19 and/or causing the regression or disappearance of chemosensory dysfunction.

A "therapeutically effective amount" can refer to an amount of a compound or its salt with or without additional agents that is effective to achieve its intended purpose. Individual patient needs may vary. Generally, the dosage required to provide an effective amount of the compound, salt thereof, or composition containing one or both of these, and which can be adjusted by one of ordinary skill in the art, will vary, depending on the age, health, physical condition, sex, weight, extent of the dysfunction of the recipient, frequency of treatment and the nature and scope of the dysfunction.

The term "subject," "host," "individual," and "patient" are as used interchangeably herein to refer to animals, typically mammalian animals. Any suitable mammal can be administered a compound, salt, or a composition as described herein or treated by a method as described herein. Non-limiting examples of mammals include humans, non-human primates (e.g., apes, gibbons, chimpanzees, orang-utans, monkeys, macaques, and the like), domestic animals (e.g., dogs and cats), farm animals (e.g., horses, cows, goats, sheep, pigs) and experimental animals (e.g., mouse, rat, rabbit, guinea pig). Mammals can be any age or at any stage of development, for example a mammal can be neonatal, infant, adolescent, adult or in utero. In some embodiments a mammal is a human. Humans can be more than about: 1, 2, 5, 10, 20, 30, 40, 50, 60, 65, 70, 75, 80, 85, 90, 95, 100, 105, 110, 115 or about 120 years of age. Humans can be less than about: 1, 2, 5, 10, 20, 30, 40, 50, 60, 65, 70, 75, 80, 85, 90, 95, 100, 105, 110, 115 or about 120 years of age. In some cases, a human can be less than about 18 years of age. In some cases, a human can be more than about 18 years of age. A mammal such as a human can be male or female.

As used herein, reference to a PDE inhibitor generally, or a specific PDE inhibitor, includes reference to any salt, solvate, ester, or polymorph of the PDE inhibitor. A "salt" can include a pharmaceutically acceptable salt. Examples of pharmaceutically acceptable salts can include those salts prepared by reaction of a compound disclosed herein with a mineral, organic acid or inorganic base, such salts including, acetate, acrylate, adipate, alginate, aspartate, benzoate, benzenesulfonate, bisulfate, bisulfite, bitartrate, bromide, butyrate, butyn-1,4-dioate, camphorate, camphorsulfonate, caproate, caprylate, chlorobenzoate, chloride, citrate, cyclo-pentanepropionate, decanoate, digluconate, dihydrogen-phosphate, dinitrobenzoate, dodecylsulfate, ethanesulfonate, formate, fumarate, glucoheptanoate, glycerophosphate, gly-colate, hemisulfate, heptanoate, hexanoate, hexyne-1,6-dio-ate, hydroxybenzoate, γ-hydroxybutyrate, hydrochloride, hydrobromide, hydroiodide, 2-hydroxyethanesulfonate, iodide, isobutyrate, lactate, maleate, malonate, methane-sulfonate, mandelate. metaphosphate, methanesulfonate, methoxybenzoate, methylbenzoate, monohydrogenphos-phate, 1-napthalenesulfonate, 2-napthalenesulfonate, nicoti-nate, nitrate, palmoate, pectinate, persulfate, 3-phenylpropi-onate, phosphate, picrate, pivalate, propionate, pyrosulfate, pyrophosphate, propiolate, phthalate, phenylacetate, phenyl-butyrate, propanesulfonate, salicylate, succinate, sulfate, sulfite, succinate, suberate, sebacate, sulfonate, tartrate, thio-cyanate, tosylate, undeconate, and xylenesulfonate. Further, a compound disclosed herein can be prepared as pharma-ceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, suc-cinic acid, malic acid, maleic acid, fumaric acid, Q-toluene-sulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxy-ethanesulfonic acid, benzenesulfonic acid, 2-naphthalene-sulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. Other acids, such as oxalic, while not in themselves pharmaceutically acceptable, can be employed in the preparation of salts useful as intermediates in obtaining a compound and/or a pharmaceutically acceptable acid addition salt. In some embodiments, a compound disclosed herein which can com-prise a free acid group reacts with a suitable base, such as the hydroxide, carbonate, bicarbonate, sulfate, of a pharmaceu-tically acceptable metal cation, with ammonia, or with a pharmaceutically acceptable organic primary, secondary or tertiary amine. Representative alkali or alkaline earth salts can include the lithium, sodium, potassium, calcium, mag-nesium, and aluminum salts and the like. Illustrative examples of bases can include sodium hydroxide, potassium hydroxide, choline hydroxide, sodium carbonate, $N^+(C_{1-4}$ alkyl)$_4$, and the like. Representative organic amines useful for the formation of base addition salts can include ethyl-amine, diethylamine, ethylenediamine, ethanolamine, diethanolamine, piperazine and the like. It may be under-stood that a compound disclosed herein can also include the quaternization of any basic nitrogen-containing groups they contain. In some embodiments, water or oil-soluble or dispersible products can be obtained by such quaternization. A compound disclosed herein can be prepared as pharma-ceutically acceptable salts formed when an acidic proton present in the parent compound either can be replaced by a metal ion, for example an alkali metal ion, an alkaline earth ion, or an aluminum ion; or coordinates with an organic base. In some embodiments, base addition salts can be also prepared by reacting the free acid form of a compound disclosed herein with a pharmaceutically acceptable inor-ganic or organic base, including, but not limited to organic bases such as ethanolamine, diethanolamine, trietha-nolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Methods of Treatment

Disclosed herein are methods for treating chemosensory dysfunction in a human. In some cases, the chemosensory dysfunction can be at least in part produced from, or occurring during or after, a coronavirus infection, such as SARS-CoV-2. In some cases, the method can comprise administering to the human a therapeutically effective amount of a phosphodiesterase (PDE) inhibitor or a phar-maceutically acceptable salt thereof to treat chemosensory dysfunction. In some cases, a coronavirus can comprise SARS-CoV-2 or a mutated form thereof, which can cause the disease COVID-19. In some cases, a PDE inhibitor or pharmaceutically acceptable salt thereof can be adminis-tered in a formulation in unit dose form.

Disclosed herein are methods of treating a condition by administering a PDE inhibitor or salt thereof as described herein. In some cases, administering can comprise admin-istering a PDE inhibitor or salt thereof in unit dose form. In some embodiments representative daily intranasal, lingual or pulmonary dosages are from about 1.0 µg to 2000 mg per day, from about 1.0 µg to 500.0 mg per day, from about 10 µg to 100.0 mg per day, from about 10 µg to about 10 mg per day, from about 10 µg to 1.0 mg per day, from about 10 µg to 500 µg per day or from about 1 µg to 50 µg per day of the active ingredient comprising a compound (i.e. PDE inhibitor). These ranges of dosage amounts represent total dosage amounts of the active ingredient per day for a given patient. In some embodiments, a daily administered dose can be less than about: 2000 mg per day, 1000 mg per day, 500 mg per day, 100 mg per day, 10 mg per day, 1.0 mg per day, 500 µg per day, 300 µg per day, 200 µg per day, 100 µg per day or 50 µg per day. In some embodiments, a daily administered dose can be at least about: 2000 mg per day, 1000 mg per day, 500 mg per day, 100 mg per day, 10 mg per day, 1.0 mg per day, 500 µg per day, 300 µg per day, 200 µg per day, 100 µg per day or 50 µg per day. In some embodiments, on a per kilo basis, suitable dosage levels of a compound can be from about 0.001 µg/kg to about 10.0 mg/kg of body weight per day, from about 0.5 µg/kg to about 0.5 mg/kg of body weight per day, from about 1.0 µg/kg to about 100 µg/kg of body weight per day, and from about 2.0 µg/kg to about 50 µg/kg of body weight per day. In some embodiments, a suitable dosage level on a per kilo basis can be less than about: 10.0 mg/kg of body weight per day, 1 mg/kg of body weight per day, 500 µg/kg of body weight per day, 100 µg/kg of body weight per day, 10 µg/kg of body weight per day, or 1.0 µg/kg of body weight per day of the compound. In some embodiments, a suitable dosage level on a per kilo basis can be at least about: 10.0 mg/kg of body weight per day, 1 mg/kg of body weight per day, 500 µg/kg of body weight per day, 100 µg/kg of body weight per day, 10 µg/kg of body weight per day of the active ingredient, or 1.0 µg/kg of body weight per day of the compound.

In some cases, the amount administered can be the same amount administered to treat a particular disease or can be an amount lower than the amount administered to treat that particular disease. The dosage may be administered once per day or several or multiple times per day. For example, a PDE inhibitor or salt thereof can be administered 2, 3, 4, 5, 6, 7, 8, 9, 10 or more times per day. In some cases, a composition can be administered once, twice or thrice in a 24-hour period. In some cases, a PDE inhibitor or salt thereof can be administered for about 1 day, 2 days, 3 days, 4 days, 5 days, 6 days, 7 days, 1 week, 2 weeks, 3 weeks, 4 weeks, 5 weeks, 1 month, 2 months, 3 months, 4 months, 5 months, 6 months, 7 months, 8 months, 9 months, 10 months, 11 months, 12 months, 1 year, 2 years, or for life. The amount of the drug administered to practice methods of the present invention will of course, be dependent on the subject being treated, the severity of the affliction, the manner of administration and the judgment of the prescribing physician. The dose used to practice the invention can produce the desired therapeutic or prophylactic effects, without producing serious side effects.

In some embodiments, administration of an effective amount of a PDE inhibitor by intranasal, lingual or pulmonary administration does not produce a detectable blood level of the PDE inhibitor. In some embodiments, administration of an effective amount of a PDE inhibitor by intranasal, lingual or pulmonary administration produces blood concentration of the PDE inhibitor that are less than about: 5 mg/dl, 2 mg/dl, 1 mg/dl, 500 µg/dl, 250 µg/dl, 100 µg/dl, 50 µg/dl, 25 µg/dl, 10 µg/dl, 5 µg/dl, or 1 µg/dl. In some embodiments, administration of an effective amount of a PDE inhibitor by intranasal, lingual or pulmonary administration produces blood concentration of the PDE inhibitor that are more than about: 2 mg/dl, 1 mg/dl, 500 µg/dl, 250 µg/dl, 100 µg/dl, 50 µg/dl, 25 µg/dl, 10 µg/dl, 5 µg/dl, or 1 µg/dl.

In some embodiments, administration of an effective amount of a PDE inhibitor or salt thereof can increase the salivary and/or nasal mucus cAMP or cGMP levels in the human by at least about: 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or about 50% relative to these levels in the human before the administering of the therapeutically effective amount of PDE inhibitor or pharmaceutically acceptable salt thereof. In some cases, the increase of the salivary and/or nasal mucus cAMP or cGMP levels are observed after about 1 to about 10 days, about 15 to about 45 days, or about 30 days of continuous treatment with the therapeutically effective amount of PDE inhibitor or pharmaceutically acceptable salt thereof.

The methods of treatment include by way of example only, oral administration, transmucosal administration, buccal administration, nasal administration such as inhalation, parental administration, intravenous, subcutaneous, intramuscular, sublingual, transdermal administration, and rectal administration. In some embodiments, the composition can be administered as a liquid nasal wash, an aerosol, a powder aerosol or a combination thereof. In some cases, the administering can comprise application intranasally in one nostril or both nostrils. In some embodiments, the gel composition can be administered to the naris. In some embodiments, the liquid composition can be administered as a nasal wash. In some cases, administering a composition can be performed during, after or both during and after a coronavirus infection.

In some cases, a composition described herein can be administered with one or more additional therapeutics. For example, a PDE inhibitor or salt thereof can be administered with a second therapy. In some cases, a second therapy can be administered concurrently or consecutively. In some cases, an additional therapeutic can comprise remdesivir, chloroquine, lopinavir, ritonavir, favilavir, interferon-beta, antivirals, oxygen or any combination thereof. In some cases, an additional therapeutic can comprise nitric oxide, a steroid, a non-steroidal anti-inflammatory drug (NSAID), or any combination thereof.

In some cases, a subject can be diagnosed (e.g. diagnosed with chemosensory dysfunction) prior to treatment with a PDE inhibitor or salt thereof. In some cases, a method of treatment can comprise diagnosing chemosensory dysfunction in a subject. In some cases, the diagnosing can comprise an in vitro assay. In some cases, chemosensory dysfunction can be diagnosed by detecting sonic hedgehog at or below a threshold level in a biological sample from the human. In some cases, a sample can be a nasal sample or a saliva sample. In some cases, chemosensory dysfunction can be diagnosed by detecting a cyclic nucleotide level at or below a threshold level in the biological sample from the human. In some cases, chemosensory dysfunction can be diagnosed by determining a detection threshold, by determining a recognition threshold, and by magnitude estimation for at least one of: pyridine, nitrobenzene, thiophene, and amyl acetate.

In some embodiments, the method of treatment is by nasal administration or inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. In some cases, a device can be a nasal spray device.

In some embodiments a subject can be a human. In some embodiments, a subject can have or can be suspected of having a disease or condition. The subject can be a patient, such as a patient being treated for a condition or a disease, such as a heart disease, hypertension, atrial fibrillation, stroke, renal failure, liver disease, cancer, diabetes, respiratory disease, asthma, chronic obstructive pulmonary disease, bronchitis, emphysema, lung cancer, cystic fibrosis, Coronavirus infection, pneumonia, pleural effusion or any combination thereof. A subject can be predisposed to a risk of developing a condition or a disease such as a respiratory disease. A subject can be in remission from a condition or a disease, such as a cancer patient. A subject can be healthy.

In some embodiments, intranasal or lingual administration of an effective amount of a PDE inhibitor increases taste or smell acuity. In some embodiments, an increase in taste or smell acuity can be at least about: 5%, 10%, 20%, 30%, 40%, 50%, 75%, or 100% compared to the untreated state. In some embodiments, taste or smell acuity can be increased to at least about: 5%, 10%, 20%, 30%, 40%, 50%, 75%, or 100% of the acuity of normal individuals. In some cases, an increase in taste or smell acuity can be measured after about 10 to about 20 days, about 15 to about 30 days, 25 days to about 50 days, 1 month to about 6 months or about 6 months to about 3 years. In some cases, an increase in taste or smell acuity can be measured after about 30 days. In some embodiments, taste or smell acuity can be measured objectively. In some embodiments, taste or smell acuity can be measured subjectively. In some cases, smell acuity can be measured by detection threshold, recognition threshold, hedonics, magnitude estimation or any combination thereof.

When administered in vivo, a compound, a salt thereof, and a composition can be administered in combination with one or more pharmaceutically acceptable carriers or excipients and in dosages described herein. A compound, a salt thereof, and a composition can be formulated as pharmaceutically acceptable a neutral (free base) or a salt form.

In some embodiments, a pharmaceutically acceptable carrier can include but are not limited to: an amino acid, a peptide, a protein, a non-biological polymer, a biological polymer, a simple sugar, a carbohydrate, a gum, an inorganic salt and a metal compound which may be present singularly or in combination. In some embodiments, a pharmaceutically acceptable carrier can comprise native, derivatized, a modified form, or combinations thereof.

In some embodiments, a composition or formulation can include an excipient. Excipients can include, but are not limited to one or more of: water, a fluidizer, a lubricant, an adhesion agent, a surfactant, an acidifying agent, an alkalizing agent, an agent to adjust pH, an antimicrobial preservative, an antioxidant, an anti-static agent, a buffering agent, a chelating agent, a humectant, a gel-forming agent, or a wetting agent. Excipients can also include a coloring agent, a coating agent, a sweetening agent, a flavoring and perfuming agent or a masking agent. A composition and formulation can include a therapeutic agent with an individual excipient or with multiple excipients in any suitable combination, with or without a carrier. In some cases, an excipient can comprise glycerol.

A therapeutically effective amount can refer to the amount of a PDE inhibitor or its salt with or without additional agents that is effective to achieve its intended purpose.

Individual patient needs may vary. Generally, the dosage required to provide an effective amount of the compound, salt thereof, or composition containing one or both of these, and which can be adjusted by one of ordinary skill in the art, will vary, depending on the age, health, physical condition, sex, weight, extent of the dysfunction of the recipient, frequency of treatment and the nature and scope of the dysfunction. Dosages can be in unit dose form.

A PDE inhibitor or its salt as described herein can be formulated as an aerosol. An "aerosol" can be any composition of a PDE inhibitor administered in an aerosolized formulation, including for example an inhalation spray, inhalation solution, inhalation suspension, a nebulized solution, or a nasal spray. Aerosolized formulations can deliver high concentrations of a PDE inhibitor directly to the airways or one or more nasal passages, in some instances with low systemic absorption. Solutions for aerosolization typically contain at least one therapeutically active PDE inhibitor or its salt dissolved or suspended in an aqueous solution that may further include one or more excipients (e.g., a preservative, a viscosity modifier, an emulsifier, or a buffering agent). The solution can act a carrier for the PDE inhibitor or its salt. In some embodiments, a preservative can methylparaben or propylparaben. These formulations can deliver a PDE inhibitor to respiratory airways, for example, one or both nares, for example, by inspiration.

In some embodiments, a PDE inhibitor can be directly applied to the nasal or lingual epithelium as a liquid, cream, lotion, ointment or gel. These can contain at least one therapeutically active PDE inhibitor or its salt. In some cases, the formulations can further include at least one excipient (e.g., a preservative, s viscosity modifier, an emulsifier, or a buffering agent) that can be formulated for administration, such as nasal drops or application with an applicator to at least a portion of one or more nasal passages. In some embodiments, a preservative can be methylparaben or propylparaben. The pH of a formulation can be maintained from about 4.5 to about 7.0, or from about 5.0 to about 7.0 or from about 5.5 to about 6.5. The osmolarity of a formulation can also be adjusted to osmolarities of from about 250 to about 350 mosm/L.

In some embodiments, the phosphodiesterase inhibitor or pharmaceutically acceptable salt can be administered using a multi-dose nasal spray device that delivers a dosage unit in a plume upon actuation. A dosage unit comprises an effective amount of a phosphodiesterase inhibitor, a pharmaceutically acceptable salt, an excipient or any combination thereof. A taste or smell disorder can be chemosensory dysfunction, anosmia, hyposmia, ageusia, hypogeusia, dysosmia, phantosmia, or a combination thereof. A dosage unit can comprise a PDE inhibitor or a pharmaceutically acceptable salt thereof, for example theophylline or a pharmaceutically acceptable salt thereof, roflumilast or a pharmaceutically acceptable salt thereof, cilostazol or a pharmaceutically acceptable salt thereof, a derivative (e.g. solvate, isomer, ester, amide, etc.) of any of these or a pharmaceutically salt thereof, or any combination thereof. A plume can have a droplet size distribution, where (a) less than about 1%, 2%, 3%, 4%, 5%, 6%, 7%, 8%, or 9% of the droplets in the plume can have a size of less than about 10 $\mu$m, (b) the droplets can have a $D_{10}$ of greater than about 12.5 $\mu$m, wherein about 6%, 7%, 8%, 9%, 10%, 11%, 12%, 13%, 14%, or 15% of the droplets in the plume have a size less than the $D_{10}$, (c) the droplets can have a $D_{50}$ of about 30 $\mu$m, wherein about 40%, 45%, 50%, 55%, or 60% of the droplets in the plume have a size less than the $D_{50}$, (d) the droplets can have a $D_{90}$ of about 75 to about 100 $\mu$m, wherein about 80%, 85%, 90%, 95%, or 99% of the droplets in the plume have a size less than the $D_{90}$, and (e) a span of the droplet size distribution can be from about 1 to about 6, wherein the span is calculated according to: $(D_{90}–D_{10})/D_{50}$. "$D_{10}$", "$D_{50}$", "$D_{90}$", and "span" are measurements of the droplet or particle size distribution of a plume.

"Magnitude estimation" or "ME" as used herein can refer to a measurement of the ability of a subject to determine the strength of a stimulant such as an odorant or a tastant.

"Recognition threshold" or "RT" as used herein can refer to a measurement of the ability of a subject to recognize the identity of a stimulant, such as an odorant or a tastant.

"Detection threshold" or "DT" as used herein can refer to a measurement of the ability of a subject to recognize exposure to a stimulant, such as an odorant or a tastant, as being pleasant or unpleasant.

"Hedonic" value or "H" value as used herein can refer to a measurement of a subject's reaction to a stimulant, such as an odorant or a tastant, as being pleasant or unpleasant.

In some cases, administering a PDE inhibitor as described herein can be used to prevent or treat diseases associated with or caused by a coronavirus. Such diseases can include, for example, anosmia, taste loss, smell loss, hyposmia, ageusia, dysosmia, parosmia, phantosmia, chemosensory dysfunction, cough, fever, fever, malaise, difficult breathing, runny nose, sore throat, nasal congestion or any combination thereof. A coronavirus infection can be caused by alpha coronavirus, beta coronavirus, gamma coronavirus, delta coronavirus, 229E coronavirus, NL63 coronavirus, OC43 coronavirus, HKU1 coronavirus, MERS-CoV, SARS-CoV, SARS-CoV-2, a mutated form thereof, or any combination of these. In some cases, a virus, such as a coronavirus can have a mutation. For example, a coronavirus comprise about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotide mutations as compared to a reference sequence. In some cases, a coronavirus can comprise a genome with more than about: 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence homology to a reference sequence. In some cases, a coronavirus can comprise a genome with less than about: 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence homology to a reference sequence. In some cases, a reference sequence can be a reference sequence from the National Center for Biotechnology Information.

In some cases, administering a PDE inhibitor as described herein can be used for patients with comorbidities. Such comorbidities can include, for example, hypertension, pulmonary hypertension, congestive heart failure, renal failure, myocardial infraction, stable, unstable and variant (Prinzmetal) angina, atherosclerosis, cardiac edema, heart disease, renal insufficiency, nephrotic edema, hepatic edema, stroke, asthma, bronchitis, chronic obstructive pulmonary disease (COPD), cystic fibrosis, dementia including Alzheimer's disease, immunodeficiency, premature labor, Parkinson's disease, multiple sclerosis, dysmenorrhea, benign prostatic hyperplasia (BPH), bladder outlet obstruction, incontinence, conditions of reduced blood vessel patency, e.g., postpercutaneous transluminal coronary angioplasty (post-PTCA), peripheral vascular disease, respiratory disease, bronchitis, emphysema, lung cancer, cystic fibrosis, pneumonia, pleural effusion, allergic rhinitis, glaucoma, malignancies and diseases characterized by disorders of gut motility, e.g, irritable bowel syndrome (IBS), rheumatoid arthritis, a bacterial infection, a fungal infection, a parasitic infection, a viral infection, HIV, systemic lupus erythematosus, psoriasis, other autoimmune diseases, Huntington's chorea, and Amyotrophic lateral sclerosis (ALS) or any combination thereof. Treatment of comorbidities can be accomplished by administering to a patient in need thereof a therapeutically effective amount of the compound and/or composition described herein.

Also disclosed herein are methods of making a composition described herein. A method of making a composition can comprise contacting a compound or its salt as described herein other ingredients as described herein (e.g. a carrier, diluent, excipient, etc.).

Example 1

A patient diagnosed or previously diagnosed with COVID-19 and having at least partial smell or taste loss associated with COVID-19 is treated with an intranasally administered a formulation comprising theophylline, which is given once per day, in each naris, for about 30 days, 60 days, or 90 days.

Administration of the formulation produces an increase in the patient's sonic hedgehog levels or cyclic nucleotide levels within about 30 days, 60 days, or 90 days. Further, this increase produces a significant increase in the patient's ability to taste and smell, thus at least partially ameliorating the smell and taste loss.

Example 2

A multi-dose nasal spray device that delivers a dosage unit in a plume upon actuation is used to treat anosmia in a subject having recovered from COVID-19, where the anosmia was caused COVID-19 and persists despite recovery from COVID-19. The multi-dose spray device is configured to provide a dosage unit of theophylline, roflumilast, cilostazol, or a combination thereof, when administered by the device intranasally. The dosage unit comprises an effective amount of the theophylline, roflumilast, cilostazol, or combination thereof in a pharmaceutically acceptable carrier comprising one or more excipients. The plume has a droplet size distribution, wherein (a) less than about 5% of the droplets in the plume having a size of less than about 10 μm, (b) a $D_{10}$ of greater than about 12.5 μm, wherein about 10% of the droplets in the plume have a size less than the $D_{10}$, (c) a $D_{50}$ of about 30 μm, wherein about 50% of the droplets in the plume have a size less than the $D_{50}$, (d) a $D_{90}$ of about 75 to about 100 μm, wherein about 90% of the droplets in the plume have a size less than the $D_{90}$, and (e) a span of from about 1 to about 6, wherein the span is calculated according to: $(D_{90}–D_{10})/D_{50}$.

After administration of the dosage unit using the multi-dose device, the patient is examined and retreated over a 30 day, 60 day, or 90 day period to monitor the treatment of the anosmia using an increase in the recognition threshold as compared to prior to the first administration.

Example 3

The Patient initially reported their sensory dysfunction as either loss of taste (i.e., flavor) and/or smell function. This subjective response was documented by objective psycho-physical measurements of olfactory function administered to each patient by use of a forced-choice, three-stimuli, step-wise-staircase technique in a fixed, controlled design (1, 2). Efficacy of this technique and results of testing were previously documented in a double-blind clinical trial (2). Four odors were used; they were pyridine (dead-fish odor), nitrobenzene (bitter-almond odor), thiophene (petroleum-like odor) and amyl acetate (banana-oil odor). Detection thresholds (DT), and recognition thresholds (RT) values for each odor were determined as previously described (1, 2). Thresholds were converted into bottle units (BU) as previously described (2) and results reported as M of correct responses for each odor in each treatment group. References: (1) Henkin, R. I. Evaluation and treatment of human olfactory dysfunction, in Otolaryngology (English, G. M. Ed.), Lippincott, Philadelphia, 1993, Vol. 2, pp. 1-86. (2) Henkin, R. I., Schecter, P. J., Friedewald, W. T., DeMets, D. L., Raff, M. S. A double blind study of the effects of zinc sulfate on taste and smell dysfunction. Amer. J. Med. Sci. 1976; 272: 285-299.

Theophylline was administered to a patient who had loss of taste and smell from COVID-19. A formulation containing 80 µg of theophylline was administered via two actuations from nasal spray device once per day. Prior to the initial administration of theophylline, a baseline smell test was performed. A follow-up smell test was performed 3 months after the initial administration. No side effects were reported. The results are shown in Table 1. The patient's detection threshold (DT) and recognition threshold (RT) for pyridine (Pyr), nitrobenzene (NO2B), thiophene (Thio) and amyl acetate (AA) was determined before treatment (pre) and after treatment (3M). In all four odorant tests, the patient's detection threshold and recognition threshold improved. An improvement of 1 bottle unit means that a patient could detect and/or recognize an odorant that was 10 times lower in concentration, when compared to baseline. For example, the recognition threshold (RT) of AA improved by 8 bottle units, also equivalent to an improvement of 8 orders of magnitude. In this case, the patient could detect a concentration of AA that was $10^8$ lower in concentration. Bottle unit numbers that are 5 or lower are considered to be in the range of normal.

TABLE 1

|  | odor | DT Pyr | DT NO2B | DT Thio | DT AA | RT Pyr | RT NO2B | RT Thio | RT AA |
|---|---|---|---|---|---|---|---|---|---|
| Patient | Pre | 11 | 11 | 10 | 11 | 11 | 12 | 10 | 12 |
| Patient | 3 M | 7 | 9 | 4 | 4 | 7 | 9 | 4 | 4 |

DT = Detection Threshold;
RT = Recognition Threshold

While exemplary embodiments have been shown and described herein, such embodiments are by way of example only. Numerous variations, changes, and substitutions can be performed on the exemplary embodiments. It should be understood that various alternatives to the embodiments described herein may be employed.

What is claimed is:

1. A method for treating chemosensory dysfunction in a human, wherein the chemosensory dysfunction is at least in part produced from, or occurring during or after, a corona-virus infection resulting from contact of the human with SARS-COV-2 or a mutated form thereof, the method comprising: administering to the human a therapeutically effective amount of a phosphodiesterase (PDE) inhibitor or a pharmaceutically acceptable salt thereof to treat the chemosensory dysfunction, wherein
the PDE inhibitor or pharmaceutically acceptable salt thereof is administered as a nasal spray in a unit dose and wherein the unit dose is in a formulation contained within a multi-dose nasal spray device.

2. The method of claim 1, wherein the formulation is a liquid formulation.

3. The method of claim 2, wherein the liquid formulation is administered as an aerosol.

4. The method of claim 2, wherein administering comprises application of the liquid formulation in one nostril or both nostrils.

5. The method of claim 1, wherein the administering is performed during or after the coronavirus infection.

6. The method of claim 5, further comprising a second administering, wherein the second administering comprises remdesivir, chloroquine, lopinavir, ritonavir, favilavir, interferon-beta, antivirals, oxygen or any combination thereof.

7. The method of claim 1, wherein the administering is at least once, twice, or thrice within a 24-hour period.

8. The method of claim 1, wherein the chemosensory dysfunction comprises anosmia, hyposmia, ageusia, dysosmia, parosmia, phantosmia or any combination thereof.

9. The method of claim 1, wherein the PDE inhibitor or pharmaceutically acceptable salt thereof is theophylline or a pharmaceutically acceptable salt thereof, roflumilast or a pharmaceutically acceptable salt thereof, cilostazol or a pharmaceutically acceptable salt thereof, a derivative of any of these, a pharmaceutically salt thereof, or any combination thereof.

10. The method of claim 1, wherein the therapeutically effective amount comprises a positive amount of less than about 10 mg, less than about 1 mg, less than about 500 µg or less than about 100 µg of the PDE inhibitor or the pharmaceutically acceptable salt thereof.

11. The method of claim 1, wherein salivary or nasal mucus cAMP or cGMP levels in the human increase by at least about 10% relative to these levels in the human before the administering, after about 30 days of continuous treatment with the therapeutically effective amount of PDE inhibitor or pharmaceutically acceptable salt thereof.

12. The method of claim 1, wherein the chemosensory dysfunction is diagnosed by detecting sonic hedgehog at or below a threshold level in a biological sample from the human, by detecting cyclic nucleotide level at or below a threshold level in the biological sample from the human, or any combination thereof.

13. The method of claim 1, wherein the formulation comprises an excipient, and wherein the excipient comprises water.

14. The method of claim 1, wherein the PDE inhibitor or pharmaceutically acceptable salt thereof is theophylline or a pharmaceutically acceptable salt thereof.

15. The method of claim 1, wherein the human is assigned male or female at birth.

16. The method of claim 15, wherein the human is from about 1 month to about 12 months old, from about 1 year to about 20 years, from about 15 years to about 50 years, from about 40 years to about 80 years, or from about 60 years to about 110 years.

17. The method of claim 15, wherein the human has a comorbidity.

18. The method of claim 17, wherein the comorbidity is selected from the group consisting of schematic heart disease, hypertension, atrial fibrillation, stroke, renal failure, liver disease, cancer, diabetes, respiratory diseases, and any combination thereof.

19. The method of claim 18, wherein the comorbidity is the respiratory disease, wherein the respiratory disease is selected from asthma, chronic obstructive pulmonary disease, bronchitis, emphysema, lung cancer, cystic fibrosis, pneumonia, pleural effusion, or any combination thereof.

* * * * *